United States Patent [19]
Wolfram

[11] Patent Number: 5,665,336
[45] Date of Patent: Sep. 9, 1997

[54] ACIDIC POST-TREATMENT OF HAIR DYED WITH DIHYDROXYINDOLE

[75] Inventor: Leszek Wolfram, Stamford, Conn.

[73] Assignee: Bristol-Myers Squibb Company, New York, N.Y.

[21] Appl. No.: 517,179

[22] Filed: Aug. 21, 1995

Related U.S. Application Data

[63] Continuation of Ser. No. 169,953, Dec. 17, 1993, abandoned, which is a continuation-in-part of Ser. No. 892,866, Jun. 3, 1992, abandoned.

[51] Int. Cl.$^6$ ............................... A61K 7/06; A61K 7/13
[52] U.S. Cl. ................................. 424/70.6; 8/441
[58] Field of Search ..................... 424/70.6, 62; 8/441

[56] References Cited

U.S. PATENT DOCUMENTS

| | | | |
|---|---|---|---|
| 3,933,421 | 1/1976 | Lewis | 8/432 |
| 4,425,132 | 1/1984 | Grollier | 8/406 |
| 4,808,190 | 2/1989 | Grollier | 8/406 |
| 5,011,500 | 4/1991 | Grollier | 8/406 |
| 5,135,544 | 8/1992 | Grollier | 8/408 |

FOREIGN PATENT DOCUMENTS

| | | | |
|---|---|---|---|
| 0378937 | 7/1990 | European Pat. Off. | |
| 2657781 | 8/1991 | France | |
| 2132642 | 7/1984 | United Kingdom | 8/431 |
| 2186891 | 8/1987 | United Kingdom | |

*Primary Examiner*—Sallie M. Gardner
*Attorney, Agent, or Firm*—Charles J. Zeller

[57] ABSTRACT

A process for altering the color of hair that has been dyed with dihydroxyindole comprising the steps of treating the dyed hair with an acidic solution for an effective amount of time and rinsing the treated hair.

10 Claims, No Drawings

ACIDIC POST-TREATMENT OF HAIR DYED WITH DIHYDROXYINDOLE

This is a continuation of U.S. Ser. No. 08/169,953 filed Dec. 17, 1993, now abandoned, which is a continuation-in-part of U.S. Ser. No. 07/892,866 abd filed Jun. 3, 1992, now abandoned.

BACKGROUND OF THE INVENTION

This invention relates to a process for altering the color of hair that has been dyed with dihydroxyindole, or a metal catalyzed dihydroxyindole system (hereinafter collectively referred to as DHI), by treating the dyed hair with an acidic solution.

Dyeing hair with DHI has many advantages: DHI produces intense haircolor, it is a relatively mild hair treatment that does not damage hair, and it is a precursor to a natural pigment, melanin—a characteristic that pleases consumers. The primary disadvantage of using DHI to dye hair is its inability to produce colors other than gray or black. Most natural haircolors are warmer, redder shades than those produced using DHI. Hence, there exists a need in the art for obtaining natural-looking haircolors using DHI dyes.

There have been a number of attempts to obtain such haircolors with DHI dyes. French Patent Application 2 657 781 (Richard) discloses a method for removing or lightening the color of DHI-dyed hair that comprises first applying a potassium permanganate solution to DHI-dyed hair and then applying a reducing agent (sodium bisulfate, sodium hydrosulfate, oxalic acid, thioglycolic acid, citric acid, or ascorbic acid). However, the haircolors produced with that method are due at least in part to the deposition of manganese dioxide on the hair. Manganese dioxide is a colorant that masks the color produced by DHI treatment. Thus it was surprising that the present invention, using an acidic solution (which may be a reducing agent) without an added colorant and absent the presence in the acidic solution of other color modifiers such as hydrogen perioxide, periodic acid and its salts, sodium hypochlorite, nitrites and the like, alone or in admixture, produces natural-looking haircolor without needing to mask the color of the DHI-dyed hair. Furthermore, permanganate is a cosmetically unacceptable colorant. It forms an intensely colored solution that stains easily and thus is very difficult to work with. In contrast, the claimed process is simple and harmless.

U.S. Pat. No. 3,194,734 (Seemuller et al.) discloses a process and composition that produce warm, natural haircolor shades by using methyl derivatives of DHI and an oxidizing agent.

U.S. Pat. No. 4,822,375 (Lang et al.) discloses a process and composition that produce warm, natural haircolor shades by using DHI derivatives.

U.S. Pat. No. 5,011,500 (Grollier et al.) discloses a process and composition that produce warm, natural haircolor shades by using indole derivatives combined with synthetic dye materials such as nitro dyes.

U.S. Pat. No. 5,021,067 (Grollier) discloses a process and composition that produce warm, natural haircolor shades by using DHI with at least one para-phenylenediamine (a synthetic dye material) disubstituted on one of the amino groups.

U.S. Pat. No. 5,053,053 (De Labbey et al.) discloses a process and a kit that produce warm, natural haircolor shades by using DHI with at least one quinone derivative (a synthetic dye material).

SUMMARY OF THE INVENTION

It is an object of this invention to provide a process for altering the color of hair dyed with DHI so that it is a more natural-looking color, without using additional masking colorants or DHI derivatives that are not involved in the biosynthetic pathway that produces melanin.

It is also an object of this invention to provide a mild and non-damaging process for altering the color of hair dyed with DHI so that it is a more natural-looking color.

It is further an object of this invention to provide a simple process for altering the color of hair dyed with DHI so that it is a more natural color.

It is further an object of this invention to provide a process that will produce a wide range of natural hair shades by altering the color of hair dyed with DHI.

In accordance with the invention, a process is provided for altering the color of hair that has been dyed with dihydroxyindole, or a metal catalyzed dihydroxyindole system, comprising the steps of treating the dyed hair with an acidic solution for an effective amount of time and rinsing the treated hair.

DETAILED DESCRIPTION OF THE INVENTION

This invention provides a process for altering the color of hair that has been dyed with dihydroxyindole, or a metal catalyzed dihydroxyindole system, comprising the steps of treating the dyed hair with an acidic solution for an effective amount of time and rinsing the treated hair. The process changes the black/dark gray haircolor that is characteristic of DHI-dyed hair to a warm, natural-looking haircolor, without the use of masking hair colorants.

Applicant does not completely understand the mechanism underlying the present invention, although it is unlikely that an oxidative event is taking place since the lightening observed on treated hair is obtained regardless of the oxidizing ability of the acid.

The incorporation of color modifiers other than the acid constituent is outside the scope of the present invention. Thus, the presence of oxidizing agents that are commonly employed to accelerate color formation of oxidative-type dyes, namely, hydrogen peroxide, periodic acid and nitrites, are inconsistent with this invention. In the present invention, the color from the DHI has previously been imparted to the hair prior to modification by the acid solution. Accordingly, the acidic solution of the present invention is substantially oxidant-free.

Melanin is the pigment that gives hair its color. As people age, there is a gradual loss of melanin from the hair, which causes hair to turn gray or, less often, white. DHI is frequently used to dye hair that has lost melanin. The process of this invention is especially effective on gray or white DHI-dyed hair, and imparts to the hair a dark gray to black coloration. Generally, the DHI-dyed hair that is post-treated with the acidic solution in accordance with this invention has a Hunter Tristimulus L value of about 25 or less, especially about 20 or less. The Hunter system is described in connection with Example 1, and is commonly employed in measuring color in the hair dye art. In accordance with the present invention, the acidic treatment lightens the color of the previously dyed hair, i.e., the L value of the post-treated hair is increased. Preferably, the change in L value is about 2.5 or more units on the L scale. The post-treatment may further have a modifying effect on the color tones of the dyed hair. Thus, changes in the a and b values (as also explained in Example 1) generally accompanying the overall lightening effect of the acidic post-treatment. Thus, an overall color change determined by the value of E (as explained in Example 1) of 3 or more units, preferably of 5 or more units, can be achieved.

Any type of acid, including citric acid, ascorbic acid, lactic acid, naphthalenesulfonic acid, or hydrochloric acid, can be used in accordance with this invention. However, citric acid and ascorbic acid are preferred, and citric acid is most preferred.

The mild acidic solutions used in the process of this invention are effective at concentrations ranging from about 0.1% to about 5%. The preferred concentration of the acidic solution will vary according to the strength of the acid used. However, it is generally preferred that the concentration of the acidic solution is about 2%.

The pH of the acidic solution may range from about pH 2 to about pH 7. However, it is preferred that the acidic solution be about pH 2 to 3.

The overall acidic solution should be mild and non-damaging to the hair. However, lower pH and higher concentration acidic solutions may produce the most desirable haircolor. Thus, a skilled person should carefully select the type of acid, the concentration of the acidic solution, and the pH of the acidic solution so as to optimize the resulting haircolor without damaging the hair.

The effective treatment time (the amount of time that the acidic solution is left on the hair in order to achieve the desired results of the process of this invention) will vary according to the acidic solution used and the type of results desired. In general, the effective treatment time will be from about 1 minute to several minutes. Although in general, the longer the solution is left on the hair, the better the haircolor result, leaving the solution on the hair for more than about one hour gives little added benefit.

A wide range of natural-looking haircolors can be achieved with the process of this invention by altering the type of acid used, the concentration of the acid, the pH of the acid, and the amount of time that the acidic solution is left on the hair.

The process of this invention may be practiced at various time intervals from the initial DHI dye treatment. The results of the process are substantially equal regardless of whether it is performed immediately after DHI dyeing or several days after DHI dyeing.

The process of this invention is equally effective on hair that has, or has not, been pre-treated with a metal catalyzed dihydroxyindole system, such as copper sulfate.

The following examples are given to further illustrate the present invention. It should be understood, however, that the invention is not limited thereto.

EXAMPLE 1

The Effect of Different Types of Acidic Solutions on the Overall Color Change of DHI-Dyed Hair Tresses Tresses of DeMeo blended medium gray hair were treated with a copper sulfate solution and dyed with a DHI composition, as described in Great Britain Patent 2 132 642 B. These tresses were then post-treated with the various acidic solutions described below. Although all of the acidic solutions were effective—the color of all the post-treated tresses turned from black to various shades of warm brown—citric acid and ascorbic acid produced the greatest effects. The results of these comparisons are set forth in Table 1.

TABLE 1

| No. | Treatment Conditions | Hunter Color Values | | | |
| | | L | a | b | E |
| --- | --- | --- | --- | --- | --- |
| 1.1 | Control (DHI-dyed tress) | 17.53 | 0.16 | −0.35 | — |
| 1.2 | 0.25M Citric Acid pH 2.03, 10 min. | 22.57 | 1.73 | 1.99 | 5.77 |

TABLE 1-continued

| No. | Treatment Conditions | Hunter Color Values | | | |
| | | L | a | b | E |
| --- | --- | --- | --- | --- | --- |
| 1.3 | 0.25M Citric Acid pH 2.03, 60 min. | 24.82 | 2.22 | 3.24 | 8.38 |
| 1.4 | 0.25M Citric Acid pH 2.03, 24 hrs. | 24.31 | 2.51 | 3.55 | 8.17 |
| 1.5 | control (DHI-dyed tress) | 17.20 | 0.19 | −0.43 | — |
| 1.6 | 0.25M Ascorbic Acid pH 2.06, 10 min. | 25.78 | 2.29 | 3.75 | 9.77 |
| 1.7 | 0.25M Ascorbic Acid pH 2.06, 60 min. | 25.78 | 3.01 | 4.18 | 10.14 |
| 1.8 | 0.25M Lactic Acid pH 2.06, 10 min. | 21.18 | 1.19 | 1.45 | 4.51 |
| 1.9 | 0.25M Lactic Acid pH 2.06, 60 min. | 22.05 | 1.71 | 2.46 | 5.85 |
| 1.10 | 0.1M 2-Naphthalenesulfonic Acid pH 2.01, 10 min. | 19.25 | 0.61 | 0.39 | 2.25 |
| 1.11 | 0.1M 2-Naphthalenesulfonic Acid pH 2.01, 60 min. | 19.30 | 0.77 | 0.67 | 2.44 |
| 1.12 | 0.1N HCl pH 1.0, 10 min. | 24.16 | 2.50 | 3.19 | 8.18 |
| 1.13 | 0.1N HCl pH 1.0, 60 min. | 24.55 | 2.77 | 3.67 | 8.80 |

Hunter values are a measure of reflected light and describe haircolor using three parameters: L, a and b. When L=0, the haircolor is black, and when L=100, the haircolor is white. The more positive "a" is, the redder the haircolor; the more negative "a" is, the greener the haircolor. The more positive "b" is, the yellower the haircolor; the more negative "b" is, the bluer the haircolor. E is the overall color change and is calculated using the formula $E = \sqrt{(\Delta L)^2 + (\Delta a)^2 + (\Delta b)^2}$.

EXAMPLE 2

The Effect of the pH of a Citric Acid Solution on the Overall Color Change of DHI-Dyed Hair Tresses Tresses of DeMeo blended medium gray hair were treated with a copper sulfate solution and dyed with a DHI composition, as described in Great Britain Patent 2 132 642 B. These tresses were then post-treated with solutions of varying pH that comprise citric acid and sodium hydroxide. Although all of the acidic solutions were effective, the best results were achieved at lower pH. The results of these comparisons are set forth in Table 2.

TABLE 2

| No. | Treatment Conditions | Hunter Color Values | | | |
| | | L | a | b | E |
| --- | --- | --- | --- | --- | --- |
| 2.1 | Untreated blended medium gray hair | 39.72 | 0.18 | 6.52 | — |
| 2.2 | Control (DHI-dyed tress) | 18.91 | 0.33 | −0.10 | — |
| 2.3 | 0.25M Citric Acid/NaOH pH 2.02, 3 min. | 23.33 | 1.96 | 2.04 | 5.17 |
| 2.4 | 0.25M Citric Acid/NaOH pH 2.02, 10 min. | 23.63 | 2.27 | 2.63 | 5.79 |
| 2.5 | 0.25M Citric Acid/NaOH pH 4.07, 3 min. | 22.76 | 1.30 | 1.44 | 4.26 |
| 2.6 | 0.25M Citric Acid/NaOH pH 4.07, 10 min. | 22.33 | 1.46 | 1.58 | 3.97 |
| 2.7 | 0.25M Citric Acid/NaOH pH 6.18, 3 min. | 17.57 | 0.28 | −0.23 | 1.35 |
| 2.8 | 0.25M Citric Acid/NaOH pH 6.18, 10 min. | 18.47 | 0.48 | −0.01 | 0.47 |

EXAMPLE 3

The Effect of Treatment Time with Citric Acid Solution on the Overall Color Change of DHI-Dyed Hair Tresses Tresses of DeMeo blended medium gray hair were treated with a copper sulfate solution and dyed with a DHI composition, as described in Great Britain Patent. 2 132 642 B. These tresses were then post-treated with citric acid solutions at pH 2.13 for varying amounts of time. Although all of the acidic solutions were effective, the best results were achieved when the solution was left on the hair for a longer time. The results of these comparisons are set forth in Table 3.

TABLE 3

| No. | Treatment Conditions | Hunter Color Values | | | |
|---|---|---|---|---|---|
| | | L | a | b | E |
| 3.1 | 0.1M Citric Acid pH 2.13, 1 min. | 22.79 | 0.68 | 1.49 | 3.12 |
| 3.2 | 0.1M Citric Acid pH 2.13, 3 min. | 26.06 | 1.11 | 2.46 | 6.47 |
| 3.3 | 0.1M Citric Acid pH 2.13, 10 min. | 27.36 | 1.72 | 3.20 | 8.06 |

The data set forth in Tables 1 and 2 also demonstrate that in general, the longer an acidic solution is left on DHI-dyed hair, the greater the effect of the solution. However, the data set forth in Table 1 show that leaving the solution on DHI-dyed hair for more than one hour does not give an added benefit.

EXAMPLE 4

The Effect of Citric Acid Solution Concentration on the Overall Color Change of DHI-Dyed Hair Tresses Tresses of DeMeo blended medium gray hair were treated with a copper sulfate solution and dyed with a DHI composition, as described in Great Britain Patent 2 132 642 B. These tresses were then post-treated with various concentrations of citric acid solutions. Although all the concentrations of citric acid solutions tested were effective—the color of all the post-treated tresses turned from black to various shades of warm brown—the higher concentrations of citric acid produced greater effects. The results of these comparisons are set forth in Table 4.

TABLE 4

| No. | Treatment Conditions | Hunter Color Values | | | |
|---|---|---|---|---|---|
| | | L | a | b | E |
| 4.1 | Control (DHI-dyed tress) | 17.61 | 0.32 | −0.44 | — |
| 4.2 | 2% Citric Acid pH 2.3 | 20.19 | 0.65 | 0.45 | 2.75 |
| 4.3 | 1% Citric Acid pH 2.8 | 19.38 | 0.38 | −0.09 | 1.81 |
| 4.4 | 0.3% Citric Acid pH 4.4 | 17.18 | 0.21 | −0.24 | 0.49 |

EXAMPLE 5

The Effect of the Time Interval from the Initial DHI Dye Treatment on the Overall Color Change of DHI-Dyed Hair Tresses Tresses of DeMeo blended medium gray hair were treated with a copper sulfate solution and dyed with a DHI composition, as described in Great Britain Patent 2 132 642 B. These tresses were then post-treated with various acidic solutions at various time intervals from the initial DHI dye treatment. The results show that the process of this invention is effective for many days after the hair was initially dyed. The data from these comparisons are set forth in Table 5.

TABLE 5

| No. | Treatment Conditions | Hunter Color Values | | | |
|---|---|---|---|---|---|
| | | L | a | b | E |
| 5.1 | Control (DHI-dyed tress) | 18.87 | 0.09 | 0.00 | — |
| | Citric Acid, 0.25M, pH 2.03, 10 min.: | | | | |
| 5.2 | Immediately After Dyeing | 25.61 | 2.69 | 3.82 | 8.17 |
| 5.3 | 1 Hour After Dyeing | 21.26 | 1.46 | 1.65 | 3.21 |
| 5.4 | 5 Hours After Dyeing | 19.76 | 1.13 | 1.08 | 1.74 |
| 5.5 | 10 Days After Dyeing | 21.09 | 1.27 | 2.20 | 3.34 |
| | Ascorbic Acid, 0.25M, pH 2.06, 10 min.: | | | | |
| 5.6 | Immediately After Dyeing | 26.58 | 2.68 | 4.04 | 9.08 |
| 5.7 | 1 Hour After Dyeing | 22.72 | 2.30 | 2.77 | 5.23 |
| 5.8 | 5 Hours After Dyeing | 23.12 | 2.21 | 3.16 | 5.70 |
| 5.9 | 10 Days After Dyeing | 23.37 | 1.89 | 3.63 | 6.06 |

EXAMPLE 6

The Effect of Treatment Time and Citric Acid Solution Concentration on the Overall Color Change of DHI-Dyed White Hair Tresses Tresses of white hair were treated with a copper sulfate solution and dyed with a DHI composition, as described in Great Britain Patent 2 132 642 B. These tresses were then post-treated with varying concentrations of citric acid solutions for varying amounts of time. The results of these comparisons are set forth in Table 6.

TABLE 6

| No. | Treatment Conditions | Hunter Color Values | | | |
|---|---|---|---|---|---|
| | | L | a | b | E |
| 6.1 | Untreated white hair | 75.92 | −2.14 | 11.47 | — |
| 6.2 | Control (DHI-dyed tress) | 24.49 | 0.21 | −3.02 | — |
| 6.3 | 0.1M Citric Acid, 10 min. | 27.63 | 1.85 | 1.05 | 5.40 |
| 6.4 | 0.1M Citric Acid, 20 min. | 29.96 | 2.43 | 1.92 | 7.70 |
| 6.5 | 0.1M Citric Acid, 40 min. | 30.25 | 2.62 | 2.55 | 8.37 |
| 6.6 | 0.25M Citric Acid, 10 min. | 32.34 | 3.25 | 2.70 | 10.18 |
| 6.7 | 0.25M Citric Acid, 20 min. | 33.30 | 3.48 | 3.24 | 11.29 |
| 6.8 | 0.5M Citric Acid, 10 min. | 30.72 | 3.05 | 2.72 | 8.93 |
| 6.9 | 0.5M Citric Acid, 20 min. | 33.11 | 3.54 | 3.48 | 11.30 |

EXAMPLE 7

The Effect of Copper Sulfate Pre-treatment on the Overall Color Change of DHI-dyed Hair Tresses that are Post-treated with an Acidic Solution Tresses of blended medium gray hair, which were not treated with copper sulfate solution but were dyed five times, in fifteen minute long treatments, with a DHI composition, were post-treated with various acidic solutions, at different pH, for different amounts of time. The effects are similar to those demonstrated for tresses that were pre-treated with copper sulfate solution. The results of these comparisons are set forth in Table 7.

TABLE 7

| No. | Treatment Conditions | Hunter Color Values | | | |
|---|---|---|---|---|---|
| | | L | a | b | E |
| 7.1 | Control (DHI-dyed tress) | 19.00 | 0.87 | 0.40 | — |
| 7.2 | 0.25M Citric Acid | 22.30 | 2.56 | 2.26 | 4.15 |

TABLE 7-continued

| No. | Treatment Conditions | Hunter Color Values | | | |
|---|---|---|---|---|---|
| | | L | a | b | E |
| 7.3 | pH 2.03, 10 min. 0.25M Citric Acid pH 2.03, 60 min. | 23.69 | 3.13 | 2.97 | 5.81 |
| 7.4 | 0.25M Ascorbic Acid pH 2.06, 10 min. | 22.74 | 2.70 | 2.44 | 4.64 |
| 7.5 | 0.1N HCl pH 1.0, 10 min. | 23.63 | 2.80 | 2.80 | 5.56 |

EXAMPLE 8

A Comparison with the Results Achieved by Prior Art DHI Masking Colorants

Three tresses of DeMeo blended medium gray hair (8a.2, 8a.3, and 8a.4) were dyed using the procedure described in French Patent Application 2 657 781, Example 6 (copper sulfate followed by DHI). Un dyed tress 8a.1 was used as a control. After treatment with copper sulfate and DHI, the haircolor of tress 8a.2 was black. DHI-dyed tress 8a.3 was subsequently treated with a permanganate dye composition and the resulting haircolor of the tress was dark gray/black. DHI-dyed tress 8a.4 was subsequently treated with the permanganate and citric acid compositions described in French Patent Application 2 657 781 and the resulting haircolor of tress 8a.4 was a dark greenish brown. The color change in tress number 8a.4 is largely due to the formation of a yellow haircolor by permanganate. The data from these comparisons are set forth in Table 8a.

TABLE 8a

| No. | Treatment Conditions | Hunter Color Values | | |
|---|---|---|---|---|
| | | L | a | b |
| 8a.1 | Untreated | 29.4 | 0.2 | 6.0 |
| 8a.2 | CuSO$_4$/DHI Treated | 9.8 | 0.1 | 0.9 |
| 8a.3 | CuSO$_4$/DHI/Permanganate Treated | 14.3 | 1.0 | 1.1 |
| 8a.4 | CuSO$_4$/DHI/Permanganate/Citric Acid Treated | 13.2 | 1.2 | 4.3 |

The effect of the permanganate was demonstrated by treating tress 8b.2 of DeMeo blended medium gray hair with a permanganate composition and by treating tress 8b.3 of DeMeo blended medium gray hair with a permanganate and citric acid composition. Tress 8b.1 of DeMeo blended gray hair was used a control. Tresses 8b.2 and 8b.3 were a yellow/green color after the treatments. If this yellow green color were superimposed on the black color that results from dyeing with DHI, the result would be the dark greenish brown observed with tress 8a.4. The data from this comparison are set forth in Table 8b.

TABLE 8b

| No. | Treatment Conditions | Hunter Color Values | | |
|---|---|---|---|---|
| | | L | a | b |
| 8b.1 | Untreated | 29.7 | 0.2 | 5.5 |
| 8b.2 | Permanganate Treated | 13.9 | 2.6 | 4.0 |
| 8a.3 | Permanganate/Citric Acid Treated | 18.1 | 2.7 | 8.1 |

EXAMPLE 9

Tresses of DeMeo blended medium gray hair may be treated with the indole derivatives disclosed in U.S. Pat. No. 5,011,500 (Grollier et al.) and by the dyeing processes disclosed therein, excluding the addition of the synthetic dye materials also disclosed therein. These tresses may then be post-treated with a 2% citric acid solution of pH 2.3 for 5 minutes. The resulting haircolor of the treated tresses will be a warm shade of brown.

It will be apparent to those skilled in the art that the invention described herein can be practiced by other than the embodiments disclosed herein, which are presented for the purposes of illustration and not of limitation, and the present invention is limited only by the claims that follow.

I claim:

1. A process for lightening the color of hair previously dyed to a gray to black coloration with dihydroxyindole, the process comprising the steps of applying an aqueous, acidic composition having a pH of about 2 to about 7 to the hair, the composition consisting essentially of an acid component with the proviso that the acid component is not periodic acid, the acid component being the sole color modifier in said composition and said composition being applied to the hair for a period of time effective to increase the Hunter L value of the dyed hair by 2.5 or more units, and rinsing the hair.

2. The process of claim 1 wherein the Hunter L value of the previously dyed hair is about 25 or less units.

3. The process of claim 2 wherein the acid is present in the composition in an amount of from about 0.1 to about 5% by weight of the aqueous composition.

4. The process of claim 3 wherein said acidic composition is applied for less than about one hour.

5. The process of claim 4 wherein the aqueous composition imparts tonality changes to the color of the hair.

6. The process of claim 4 wherein the acid is selected from the group consisting of citric acid, ascorbic acid, lactic acid, tartaric acid, naphthalenesulfonic acid, hydrochloric acid and mixtures thereof.

7. The process of claim 4 wherein the overall color change between the dyed and treated hair as determined by the parameter E is at least 3.

8. The process of claim 6 wherein said acidic composition is applied for less than about thirty minutes.

9. The process of claim 5 wherein the acid is selected from the group consisting of citric acid, ascorbic acid, lactic acid, tartaric acid, naphthalenesulfonic acid, hydrochloric acid and mixtures thereof.

10. The process of claim 9 wherein said acidic composition is applied for less than about thirty minutes.

* * * * *